United States Patent
Liang et al.

(10) Patent No.: US 12,053,309 B2
(45) Date of Patent: Aug. 6, 2024

(54) WASTE COLLECTION DEVICE, DOCKING DEVICE AND WASTE COLLECTION AND DISPOSAL SYSTEM

(71) Applicant: AMSINO MEDICAL (SHANGHAI) CO., LTD., Shanghai (CN)

(72) Inventors: Hongqi Liang, Shanghai (CN); Richard Ya Lee, Shanghai (CN)

(73) Assignee: AMSINO MEDICAL (SHANGHAI) CO., LTD., Shanghai (CN)

( * ) Notice: Subject to any disclaimer, the term of this patent is extended or adjusted under 35 U.S.C. 154(b) by 307 days.

(21) Appl. No.: 17/430,568

(22) PCT Filed: Aug. 28, 2019

(86) PCT No.: PCT/CN2019/102936
§ 371 (c)(1),
(2) Date: Aug. 12, 2021

(87) PCT Pub. No.: WO2020/168703
PCT Pub. Date: Aug. 27, 2020

(65) Prior Publication Data
US 2022/0133424 A1   May 5, 2022

(30) Foreign Application Priority Data

Feb. 18, 2019 (CN) .................. 201910119500.X
Jun. 6, 2019 (CN) .................. 201910489524.4
(Continued)

(51) Int. Cl.
*A61B 50/13* (2016.01)
*B08B 3/04* (2006.01)
*F16L 27/08* (2006.01)

(52) U.S. Cl.
CPC ............. *A61B 50/13* (2016.02); *B08B 3/04* (2013.01); *F16L 27/0804* (2013.01)

(58) Field of Classification Search
CPC ......... F16L 27/0804; B08B 3/04; A61B 50/13
See application file for complete search history.

(56) References Cited

U.S. PATENT DOCUMENTS

| 2002/0092580 A1 | 7/2002 | Miller et al. |
| 2005/0187529 A1 | 8/2005 | Reasoner et al. |

(Continued)

FOREIGN PATENT DOCUMENTS

| CN | 109999229 A   | 7/2019 |
| WO | 2020168936 A1 | 8/2020 |
| WO | 2020182198 A1 | 9/2020 |

OTHER PUBLICATIONS

EP19915866.8—Extended European search report is enclosed mailed on Dec. 8, 2022, 6 pages.
(Continued)

*Primary Examiner* — Jason K Niesz
(74) *Attorney, Agent, or Firm* — Getech Law LLC; Jun Ye

(57) ABSTRACT

A waste collection device and a docking device are provided for collecting waste generated in a medical process. The waste collection device is docked with the docking device to discharge the waste. The waste collection device comprises a portable cart; at least one waste collection container mounted to the portable cart and configured to store waste generated in a medical process; a mating bracket mounted to the portable cart and configured to mate with the docking device; two collection end connectors attached to the mating bracket and connected to the at least one waste collection container; and two floating sleeve heads mounted to the mating bracket and correspondingly sleeved on the two collection end connectors. The floating sleeve heads can guide docking end connectors to connect with the corresponding collection end connectors so that said connectors (Continued)

are accurately connected, and the invention has a simple structure and low manufacture cost.

20 Claims, 11 Drawing Sheets

(30) Foreign Application Priority Data

Jun. 24, 2019 (CN) .......................... 201910119988.6
Jun. 24, 2019 (CN) .......................... 201910119989.0

(56) References Cited

U.S. PATENT DOCUMENTS

| 2010/0036335 | A1* | 2/2010 | Murray | ................... | A61M 1/74 |
| | | | | | 604/319 |
| 2015/0224237 | A1* | 8/2015 | Reasoner | ............. | A61B 5/6887 |
| | | | | | 604/320 |

OTHER PUBLICATIONS

PCT/CN2019/102936—International Search Report and Written Opinion mailed on Mar. 23, 2020, 26 pages.
CN201910119500.X—First Office Action mailed on Apr. 22, 2023, 18 pages.
CN201910119989.0—Rejection Decision mailed on May 17, 2023, 6 pages.

* cited by examiner

WASTE COLLECTION DEVICE, DOCKING DEVICE AND WASTE COLLECTION AND DISPOSAL SYSTEM

CLAIM OF PRIORITY

This application is a 371 of international PCT/CN2019/102936, filed Aug. 28, 2019, which claims the benefit of priority from Chinese Patent Application No. 201910119500.X, filed Feb. 18, 2019, which claims the benefit of priority from Chinese Patent Application No. 201910489524.4, filed Jun. 6, 2019, which claims the benefit of priority from Chinese Patent Application No. 201910119988.6, filed on Jun. 24, 2019 at China National Intellectual Property Administration, entitled "WASTE COLLECTION DEVICE AND WASTE COLLECTION AND DISPOSAL SYSTEM", and from Chinese Patent Application No. 201910119989.0, filed on Jun. 24, 2019 at China National Intellectual Property Administration, entitled "DOCKING DEVICE", which are incorporated by reference herein in their entirety.

TECHNICAL FIELD

The invention relates to a waste collection device, a docking device, and a waste collection and disposal system, which are used to collect and process waste materials generated during a medical procedure, and to a docking device for docking with a waste collection device in a waste collection and disposal system for collection and treatment of waste materials generated during a medical procedure.

BACKGROUND

Waste in a liquid, semi-solid, and solid form and the like is inevitably generated in the course of performing a specific surgery. Specially, such waste includes human fluids, such as blood, and the perfusion solution introduced into a site in the body during a surgery. In addition, solid and semi-solid waste generated during a surgery includes tissue fragments and small pieces of surgical material that may be remained at the body site. In an ideal condition, the waste will be collected once it is generated, so that it will neither contaminate the surgical site nor become biohazard substances in the operating room or other location where a surgical procedure is performed.

There exist many types of waste collection systems for medical staffs to collect medical waste generated in a surgical procedure during or after the surgical procedure. The main principle thereof is that the waste generated at a surgical site is sucked into a specific collection container through a suction force generated by a vacuum source. That is, after the system is actuated, a suction force generated by a vacuum source reaches the surgical site, so that the waste is sucked into a specific collection container through a tube line contacted with the surgical site.

In the prior art, in a medical waste collection and disposal system, waste materials are collected in a waste collection container which is connected to a vacuum source. The waste collection container is generally mounted on a portable cart with wheels for easy transportation. Generally speaking, during the procedure of suction, the waste collection container needs to be emptied when the storage volume of the waste in the waste collection container reaches a predetermined volume. The approach used in the early existing technology is to push the waste collection device to a docking station, and make it emptied and cleaned. After the waste collection unit is docked to the docking station, emptying the unit starts to be performed. Once emptied, the waste collection container will be cleaned by a cleaning system through disinfection and cleaning. In a series of medical procedures, each procedure requires such an "emptying", and such frequent operations that the waste collection device is pushed to the docking station each time will cause a lot of inconvenience to users and affect a medical process. It has thus developed a transfer device specially used for transporting waste from the waste collection device to the docking station against this technical defect, that is, a docking device for specially transporting waste in the waste collection device. The docking device includes two connectors coupled with two connectors in the waste collection device to form fluid communication paths. One fluid path is used to transfer the waste from the waste collection device to the docking device, and the other fluid path is used to clean the waste collection container in the waste collection device.

In an example of the prior art, the docking device usually includes two connectors to be automatically coupled with the two connectors of the waste collection device. The main way of the automatic coupling is that a rough position matching for the docking device and the waste collection device is firstly performed, and after the two being roughly connected, the two connectors of the docking device can move at most in six directions such as upward, downward, front, back, left, and right directions by means of actuated components at the docking device end to align the two connectors of the docking device with the two connectors of the waste collection device. Since the connectors in the prior art can only move in the upward, downward, front, back, left, and right directions at most, the directions of the correction can only be upward, downward, left, and right directions. After the alignment in the upward, downward, left, and right directions, the connectors of the docking device can be inserted by forward and backward movement. In the prior art, the structure which realizes the six-direction movement of the connectors at the docking device end requires a bracket capable of moving in four directions, which needs to be constructed by a plurality of elastic members and structural members, with the addition of a stepping motor for carrying out the movement in other two directions. Said structure is complex, costs high, and the connectors can only be inserted after the docking device and the waste collection device are very accurately aligned, that is, the insertion operation of plugs can only be performed after the docking connectors of both the docking device and the waste collection device has completed an alignment before their contacts, and the operation of such alignment cannot be continued after the plug is in contact with the socket. The structure not only requires a complicated alignment operation, but also increases the complexity and cost of the device. At the same time, where a misalignment occurs, damage to the connectors will be caused due to the low fault-tolerant rate during the docking process of the two connectors of the docking device and the two connectors of the waste collection device.

SUMMARY OF THE INVENTION

The technical problem to be solved by the embodiments of the present invention is to provide a waste collection device that can automatically perform an alignment and complete the docking during the process of docking. The waste collection device has the advantage of simple structure and can save costs of both manufacturing and materials.

In order to solve the above technical problems, a waste collection device is provided according to the embodiments of the present invention. The waste collection device is utilized to collect waste generated in a medical process and dock with a docking device to discharge the waste. The waste collection device includes:

a portable cart;

at least one waste collection container mounted to the portable cart and configured to store waste generated in medical procedures;

a mating bracket mounted to the portable cart and configured to mate with the docking device;

two collection end connectors attached to the mating bracket and respectively connected to the at least one waste collection container, wherein to discharge the waste in the waste collection container, and the other is used to introduce a cleaning solution for cleaning the at least one waste collection container; and two floating sleeve heads mounted to the mating bracket and correspondingly sleeved on the two collection end connectors, wherein the floating sleeve heads are used to guide docking end connectors in the docking device to connect with the corresponding collection end connectors, and wherein the floating sleeve heads are floatingly moveable relative to the mating bracket and guide the docking end connectors to engage with the corresponding collection end connectors.

Further, after the docking end connectors and the corresponding collection end connectors are connected, the floating sleeve head returns to an initial position.

Further, the mating bracket includes a fixed plate and a guide plate. The two floating sleeve heads are mounted to the fixed plate. The guide plate and the fixed plate form a mating space for receiving a mating head part in the docking device.

Further, the fixed plate includes two fixed through holes for mounting the two floating sleeve heads.

Further, the fixed plate further includes two limiting fixed sleeves mounted in the two fixed through holes respectively.

Further, the floating sleeve head includes a floating sleeve sleeved on the collection end connector and passed through the limiting fixed sleeve. The floating sleeve includes a guide port for guiding the docking end connector and a floatable port for mating with the limiting fixed sleeve in an initial state. When the docking end connector of the docking device is not inserted, the floatable port is mated with the limiting fixed sleeve, and the floating sleeve head is in the initial position. During the process of the docking end connector being inserted, the floatable port moves relative to the limiting fixed sleeve and guides the docking end connector to align with the corresponding collection end connector.

The floating sleeve head also includes a first elastic member positioned between the guide port and the limiting fixed sleeve. The first elastic member is used to limit the range of movement of the floating sleeve during the process of the docking end connector being inserted and return the floating sleeve head back to the initial state after the docking end connector is removed.

Further, an outer tube is also disposed at the guide port of the floating sleeve, and the outer tube has a limiting edge to be mated with the mating head part.

Further, the outer tube and the floating sleeve form a limiting groove for limiting the other end of the first elastic member.

Further, the limiting fixed sleeve includes a docking top for docking with the floatable port in the initial state, a first limiting internal cavity for limiting one end of the first elastic member, and a second limiting internal cavity for accommodating the guide port and limiting the position of the guide port.

Further, the docking top includes a first guide recess in cone shape for guiding the floatable port.

Further, the floatable port is a retaining ring detachably fixed to the floating sleeve, and the retaining ring includes a cone-shaped guide portion for mating with the first guide recess.

Further, the first elastic member is a first spring sleeved on the floating sleeve.

Further, a first lock washer is interposed between the limiting fixed sleeve and the fixed plate for fastening the limiting fixed sleeve.

Further, a second lock washer is further interposed between the floating sleeve and the retaining ring for fastening the retaining ring.

Further, the guide port includes a second guide recess in cone shape.

Further, the floating sleeve is coupled with the collection end connector so that the collection end connector can move along with the floating sleeve.

Further, the floating sleeve and the connector end sleeve are in snap-fit connection.

Correspondingly, a docking device is also provided according to the embodiments of the present invention. The docking device is used in a waste collection and disposal system for transporting waste generated in a medical process collected by the waste collection device in the system. The docking device includes:

a mating head part for mating with a mating bracket in the waste collection device;

at least one actuating component positioned in the mating head part and capable of being freely stretched out and retracted in a particular direction;

two docking end connectors connected to the at least one actuating component, and when the mating head part is aligned with the mating bracket, the actuating component acts to make the docking end connectors in contact with floating sleeve heads in the waste collection device to form a docking connection;

wherein the mating head part includes a mating plate, and the mating plate includes two guide bayonets for retaining the floating sleeve heads, and the docking end connector can pass through the guide bayonets.

Further, the guide bayonet is substantially U-shaped.

Further, the mating plate includes two correction sides, which are wedge-shaped structures.

Further, the number of the actuating components is two, and they are connected to the two docking end connectors respectively.

Further, the actuating component is a pneumatic pump.

Further, the actuating component is a stepping motor.

Further, the mating head part further includes an attractor, and the attractor is an electromagnet.

Further, the docking device further includes two guiding sideplates disposed on both sides of the mating head part for mating with the waste collection device.

Further, the guide sideplate is provided with a plurality of guide rails, and the guide rails are made of flexible materials.

Further, the guide bayonet has an inner end with a curved surface, and two sides of wedge-shaped structures so that the opening width from the front end to the inner end of the bayonet is gradually reduced.

Further, the guide bayonet includes a first upper locking groove and a second upper locking groove. The first upper locking groove is used to guide the floating sleeve head, and the second upper locking groove is used to limit the position of the floating sleeve head.

Further, one of the two docking end connectors is connected to a discharge interface for discharging waste, and the other is connected with a cleaning interface for infusing a cleaning solution.

Correspondingly, a waste collection and disposal system is also provided according to the embodiments of the present invention. The waste collection and disposal system includes:

a waste collection device as described above;

a docking device, which includes a mating head part for mating with the mating bracket of the waste collection device; at least one actuating component positioned in the mating head part and capable of being freely stretched out and retracted in a particular direction; two docking end connectors connected to the at least one actuating component, and when the mating head part is aligned with the mating bracket, the actuating component acts to make the docking end connector in contact with the floating sleeve head, and the docking end connector makes the floating sleeve move floatingly to guide the docking end connector to align with the collection end connector.

Further, the docking device further includes a suction pump for sucking the waste in the waste collection device.

Further, the number of the actuating components is two, and they are connected to the two docking end connectors respectively.

The beneficial effects by implementing the embodiments of the present disclosure can comprise as follows:

First of all, in the waste collection device according to the embodiment of the present invention, the docking end connectors of the docking device are first mated with the floating sleeve heads, and then the collection end connectors and the docking end connectors are coupled. After the docking end connector is inserted into the corresponding floating sleeve head, the floating sleeve head are floatingly movable to guide the docking end connector into the floating sleeve head, and the docking end connector is gradually aligned with the collection end connector. Due to the suspension movement of the floating sleeve head, the docking end connector will not cause an impact on the floating sleeve head and will also not bring about a displaced collision with the collection end connector to cause wear, even if the docking end connector and the floating sleeve head are not completely aligned. That is, in the process of the waste collection device being docked to the docking device, there can be a relatively high fault tolerance to position, which can not only improve the accurate rate of docking, but also facilitate user friendly operation, and at the same time it can also reduce the damage caused by the imprecise alignment between the collection end connectors and the docking end connectors.

Secondly, the waste collection device in the embodiments of the invention can have a simple and low complex structure for achieving position guidance and correction, which requires less raw materials, is easy to manufacture, and can reduce costs.

DESCRIPTION OF THE DRAWINGS

To describe the technical solutions of the embodiments of the present disclosure more clearly, the following briefly introduces the accompanying drawings required for describing the embodiments of the present disclosure or the prior art. Apparently, the accompanying drawings described below illustrate merely some embodiments of the present disclosure, and one of ordinary skill in the art may derive other drawings from the accompanying drawings without creative efforts.

DETAILED DESCRIPTION

The description of the following embodiments is to illustrate specific implementable embodiments in the present disclosure with reference to accompanying drawings. The directional terms mentioned in the present disclosure, such as "upper", "downward", "front", "rear", "left", "right", "inner", "outer", "side", etc., are only directions by referring to the accompanying drawings. Therefore, the directional terms herein are used to illustrate and understand the present invention, and are not intended to limit the scope of the present invention.

In order to make the objectives, technical solutions and advantages of the present disclosure clearly and fully understandable, the present disclosure will be further described in detail below with reference to the accompanying drawings.

Figure 1:
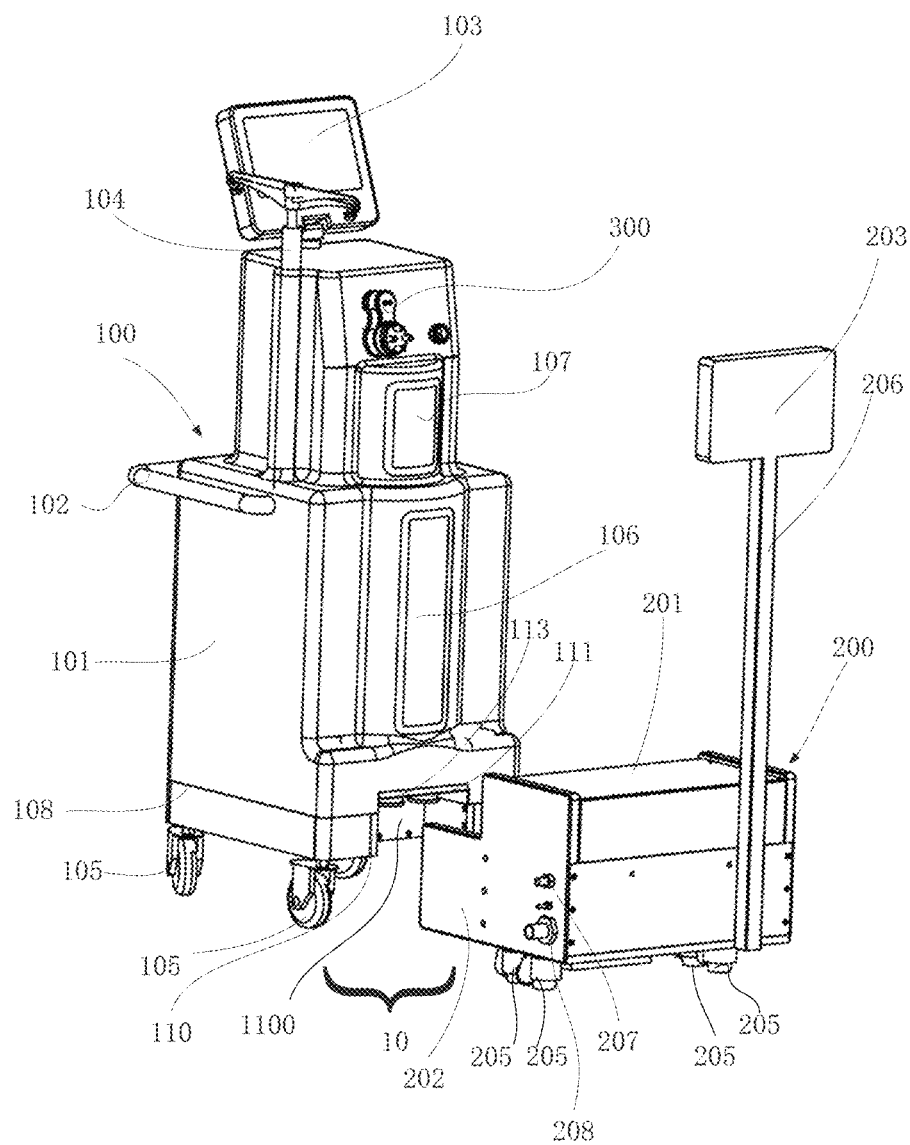
FIG. 1 shows a waste collection and disposal system where the waste collection device and a docking device are in an undocked state.
Figure 2:
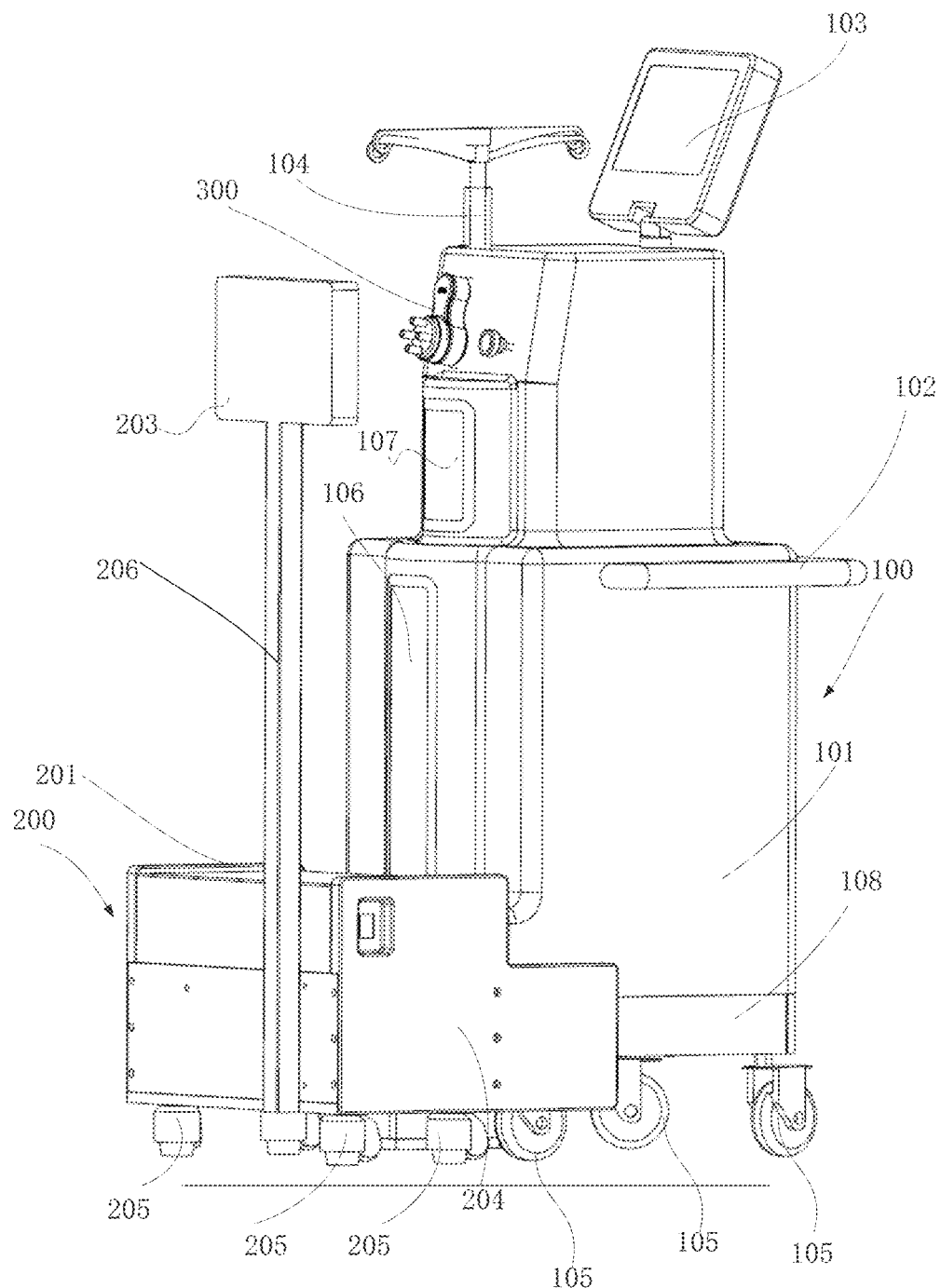
FIG. 2 shows a waste collection and disposal system where the waste collection device and docking device are in a docked state.

As shown in FIGS. 1 to 4, FIGS. 1 and 2 show a waste collection and disposal system 10, which includes a waste collection device 100 and a docking device 200. FIG. 1 shows the waste collection and disposal system 10 where the waste collection device 100 and the docking device 200 are in an undocked state. FIG. 2 shows the waste collection and disposal system 10 where the waste collection device 100 and the docking device 200 are in a docked state. The waste collection device 100 can be connected to an external suction tube line (not shown) through a manifold 300, and the external suction tube line can be connected to a suction connector (not shown). The suction connector may be a separate connector or be attached to a surgical device. The suction force at the suction connector can make the waste transported to the waste collection device 100 through the external suction tube line for storage. After the docking device 200 is docked with the waste collection device 100, the waste in the waste collection device 100 can be emptied by utilizing the docking device 200, and at the same time, a clean passage for cleaning a waste collection container 109 in the waste collection device 100 can be formed. The discharge circuit control and the flushing circuit control used in the waste collection and disposal system 10 have been known by those skilled in the art, and will not be repeatedly described herein.

The waste collection device 100 is disposed in the waste collection and disposal system 10, and is used to collect waste generated in the medical process, and to dock with the docking device 200 to discharge waste. Referring to FIGS. 1 and 2, the waste collection device 100 includes a portable cart 108, at least one waste collection container 109 mounted to the portable cart 108, a mating bracket 110, two collection end connectors 112, 114, and two floating sleeve heads 111, 113.

The portable cart 108 can move by utilizing a first wheel 105 mounted thereon, and the number of wheels is four. Specifically, the portable cart 108 also includes a collection end housing 101, a pusher 102 disposed in the middle part of the housing 101, and a collection end display screen 103 is disposed on the top of the collection end housing 101. Preferably, the display screen 103 can be foldably disposed on the collection end housing 101. The portable cart 108 is also provided with a supported hanger rod 104.

Figure 3:
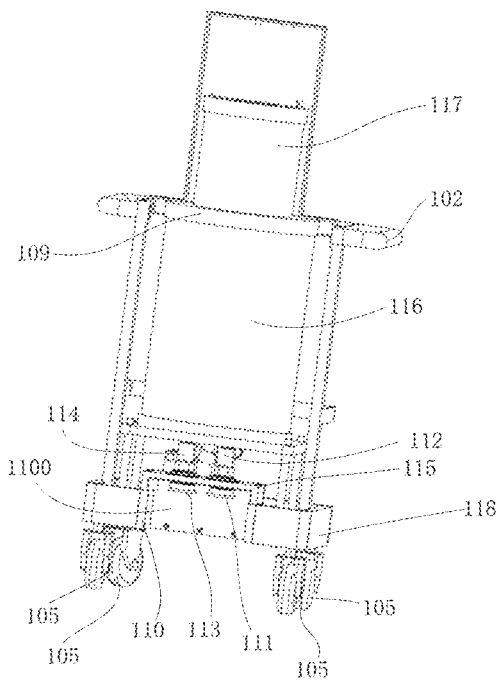
FIG. 3 is a schematic front view of the internal structure of the waste collection device according to the present disclosure.

Referring to FIG. 3, FIG. 3 is a schematic front view of the internal structure of the waste collection device according to the present disclosure. The waste collection container 109 is mounted to the portable cart 108 and is used to store waste generated in the medical process. One waste collection container 109 is provided in this embodiment. The waste collection container 109 has a first storage bin 116 and a second storage bin 117, wherein the volume of the first storage bin 116 is greater than the volume of the second storage bin 117. The number of waste collection containers may also be two, that is, the first storage bin 117 and the second storage bin 117 are separated into two independent waste collection containers. The waste collection container 109 is mounted inside the collection end housing 101. Preferably, the collection end housing 101 includes a corresponding observation window for observing the waste in the waste collection container 109, such as the level of liquid or color. In the embodiment, a first observation window 106 and a second observation window 107 are correspondingly arranged for observing the first storage bin 116 and the second storage bin 117 respectively.

A mating bracket 110 is mounted to the bottom frame 118 of the portable cart 108 for mating with the docking device 200. The mating bracket 110 has a mating space 1100 for receiving a mating head part 210 in the docking device 200.

Figure 4:
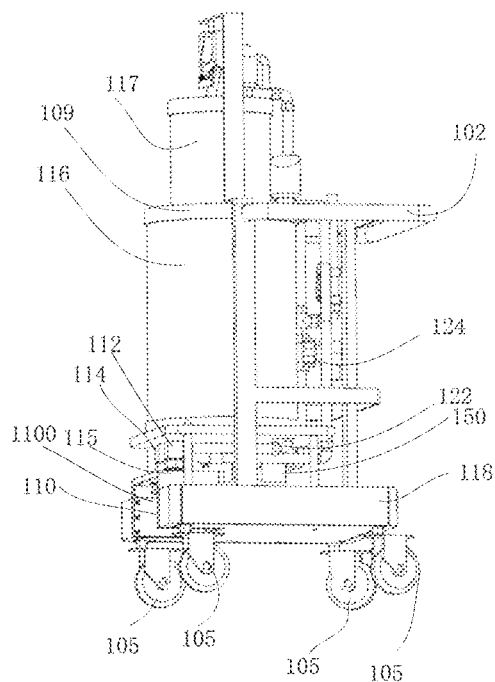
FIG. 4 is a schematic side view of the internal structure of the waste collection device according to the present disclosure.

The two collection end connectors 112, 114 are attached to the mating bracket 110 and are respectively connected to at least one waste collection container 109. One collection end connector 112 is used to discharge the waste in the waste collection container 109, and the other collection end connector 114 is used to introduce a cleaning solution for cleaning at least one waste collection container 109. For sake of being easily distinguished in the embodiment, the collection end connector 112 for discharging waste in the waste collection container 109 is referred to as a first collection end connector 112, and the collection end connector 114 for introducing a cleaning solution for cleaning the waste collection container 109 is referred to as a second collection end connector 114. Referring to FIG. 4, FIG. 4 is a schematic side view of the internal structure of the waste collection device according to the present disclosure. As shown in FIG. 4, the first collection end connector 112 is connected to the waste collection container 109 through a discharge tube 122. Specifically, the first collection end connector 112 is connected to the first storage bin 116 of the waste collection container 109 through the discharge tube 122, that is, one end of the discharge tube 122 is connected to the first collection end connector 112, and the other end is connected to the bottom of the first storage bin 116. The second collection end connector 114 is connected to the second storage bin 117 of the waste collection container 109 through a cleaning tube 124, that is, one end of the cleaning tube 124 is connected to the second collection end connector 114, and the other end is connected to the top of the second containing bin 117.

The two floating sleeve heads 111, 113 are mounted to the mating bracket 110, and are respectively sleeved on the two collection end connectors 112, 114. The two floating sleeve heads 111, 113 are used to guide two docking end connectors 212, 214 in the docking device 200 to be connected with the two collection end connectors 112 and 114 respectively. The two floating sleeve heads 111 and 113 are floatingly moveable relative to the mating bracket 110 and guide the two docking end connectors 212 and 214 to couple with the two collection end connectors 112 and 114. When the docking end connectors 212, 214 of the docking device 200 are not inserted, the corresponding floating sleeve heads 111, 113 are in an initial position. During the process of the docking end connectors 212, 214 being inserted, the floating sleeve heads 111, 113 are floatingly moveable relative to the mating bracket 110 and guide the two docking end connectors 212 and 214 to couple with the collection end connectors 112 and 114.

In this embodiment, the waste collection device 100 can be described as including a portable cart 108, at least one waste collection container 109 mounted to the portable cart 108, and a mating bracket 110. The waste collection device 100 further includes a first collection end connector 112 and a second collection end connector 114 attached to the mating bracket 110. Both the first collection end connector 112 and the second collection end connector 114 are connected to the at least one waste collection container 109, wherein the first collection end connector 112 is used to discharge the waste in the at least one waste collection container 109, and the second collection end connector 114 is used to introduce a cleaning solution for cleaning the at least one waste collection container 109.

The waste collection device 100 further includes a first floating sleeve head 111 and a second floating sleeve head 113 attached to the mating bracket 110. The first floating sleeve head 111 is sleeved on the first collection end connector 112, and the second floating sleeve head 113 is sleeved on the second collection end connector 114. The first floating sleeve head 111 is used to guide the first docking end connector 212 of the docking device 200 to connect with the first collection end connector 112, and the second floating sleeve head 113 is used to guide the second docking end connector 214 of the docking device 200 to connect with the second collection end connector 114. When the first docking end connector 212 and the second docking end connector 214 are not correspondingly inserted in the first floating sleeve head 111 and the second floating sleeve head 113, the first floating sleeve head 111 and the second floating sleeve head 113 are in an initial position. During the process of the first docking end connector 211 and the second docking end connector 214 being inserted, the first floating sleeve head 111 and the second floating sleeve head 113 are floatingly moveable relative to the mating bracket 110 and guide the corresponding alignment and coupling of the first docking end connector 212 and the second docking end connector 214 with the first collection end connector 112 and the second collection end connector 114.

Referring to FIGS. 1 to 12, the waste collection and disposal system 10 also includes a docking device 200, which includes a mating head part 210, at least one actuating component such as two actuating components 231, 241 as an example, and two docking end connectors 212, 214.

The mating head part 210 is used to mate with the mating bracket 110 of the waste collection device 100. Specifically, the mating head part 210 is inserted into the mating space 1100 of the mating bracket 110 to realize a preliminary alignment of the docking device 200 and the waste collection device 100.

At least one actuating component 231, 241 is disposed in the mating head part 210 and can move freely in a specific direction.

The two docking end connectors 212, 214 are connected to the at least one actuating component 231, 241. And when the mating head part 210 is aligned with the mating bracket 110, the actuating components 231, 241 implement actions so that the docking end connectors 212, 214 is contacted with the floating sleeve heads 111, 113, and can thus form a docking connection. The docking end connectors 212, 214 make the floating sleeve heads 111, 113 move floatingly so as to guide the docking end connectors 212, 214 to be coupled with the collection end connectors 112, 114. In this embodiment, one docking end connectors 212 is used to transport the waste in the waste collection container 109, and the other docking end connector 214 is used to transport a cleaning solution for cleaning the waste collection container 109. In order to facilitate the distinction, the docking end connector 212 for transporting the waste in the waste collection container 109 is referred to as the first docking end connector 212, and the first docking end connector 212 can be docked with the first collection end connector 112 to form a waste discharge passage. The second docking end connector 214 can be docked with the second collection end connector 114 to form a passage of cleaning the waste collection container 109. Specifically, the second docking end connector 214 is connected to a cleaning interface 207 configured to infuse a cleaning solution.

In this embodiment, two actuating components 231 and 241 are correspondingly provided. The one attached to the first docking end connector 212 is called as the first actuating component 231, and the one attached to the second docking end connector 214 is called as the two actuating component 241. The two actuating components 231, 241 can be pneumatic pumps or stepping motors, or other members or mechanical structures capable of carrying out retracting and stretching movements. Pneumatic pumps are preferably utilized in the embodiment so as to reduce the circuit components used in the docking device 200 and thus reduce circuit faults, which meanwhile reduce potential risks of complex circuits to the device. On the other hand, due to its speed and strength in a pushing process, the pneumatic pump is more conducive to the guiding of the floating sleeve heads 111, 113 to the docking end connectors 212, 214. The docking device 200 also includes a suction pump (not shown), which is used to connect to the first docking end connector 212 and discharge the waste sucked by the first docking end connector 212 through a discharge connector 208.

Figure 5:
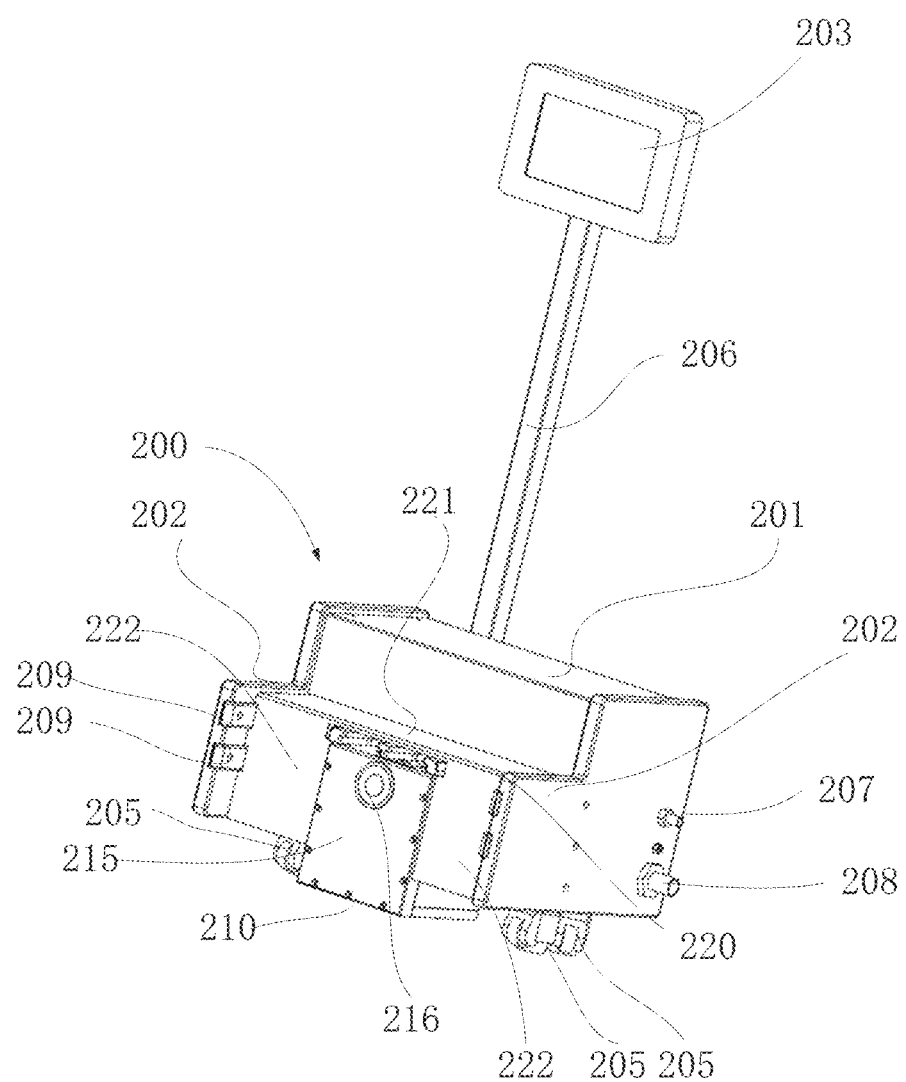
FIG. 5 is a schematic view illustrating the structure of the docking device not being received in a baffle according to the present disclosure.
Figure 6:
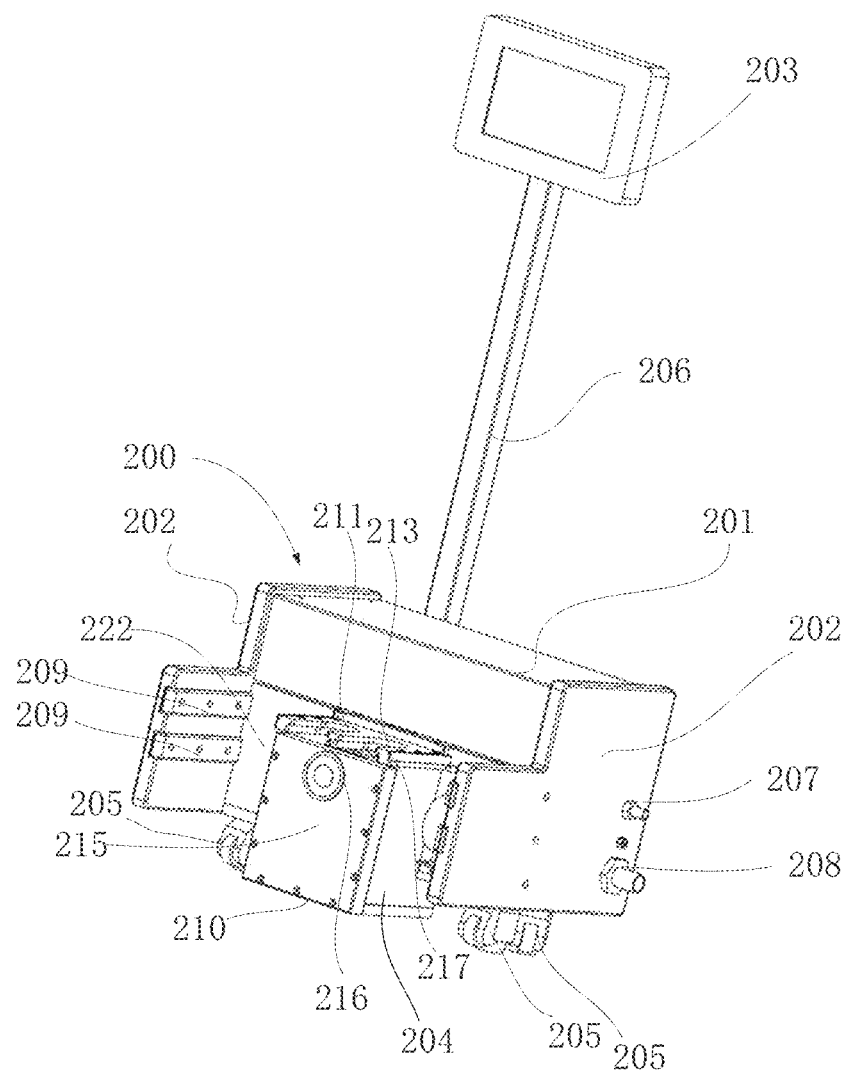
FIG. 6 is a schematic view illustrating the structure of the docking device being received in a baffle according to the present disclosure.

Referring to FIGS. 5 and 6, the docking device 200 further includes a housing 201. The housing 201 includes two guide sideplates 202, the position of the front end of the guide sideplate 202 is approximately the same as or protrudes beyond the position of the front panel 215 of the mating head part 210. Referring to FIGS. 2 and 3, the two guide sideplates 202 are correspondingly mated with the bottom frame 118 of the portable cart 108. At the same time, in order to conveniently and accurately connect the docking device 200 with the waste collection device 100, guide rails 209 are also disposed on the inner side of the guide sideplate 202. Preferably, each guide sideplate 202 may be provided with 2 to 4 guide rails 209, which are made of flexible material and can be used as a buffer strip so as to prevent the docking device 200 and the waste collection device 100 from impact and wear being caused therefor.

The mating head part 210 includes a front panel 215 on which an attractor 216 is mounted. The attractor 216 is an electromagnet. When the mating head part 210 of the docking device 200 is roughly fitted into the mating space 1100 of the mating bracket 110, the attractor 216 is turned on. The attractor 216 provides a preset attraction force which can make the mating head part 210 of the docking device 200 quickly and automatically mated with the mating bracket 110 of the waste collection device 100 to form a tight connection structure.

Figure 10:
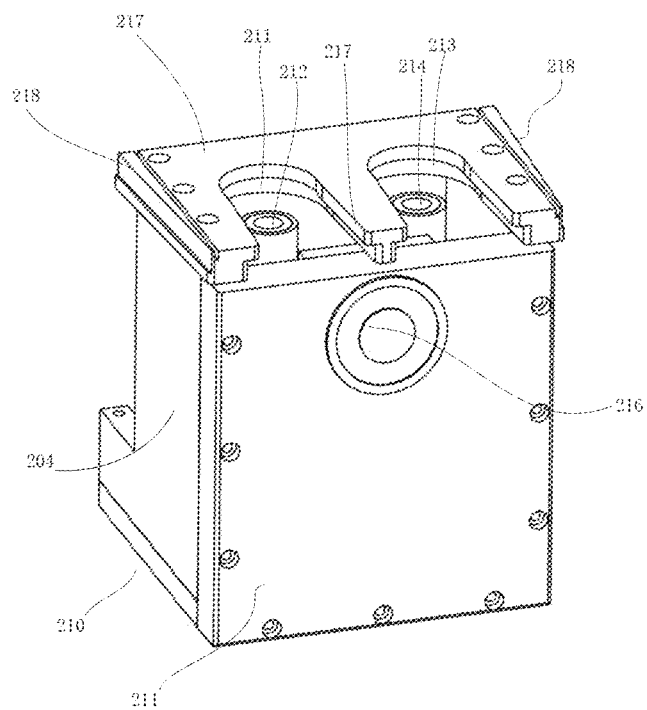
FIG. 10 is a schematic structural view of a mating head part.
Figure 11:
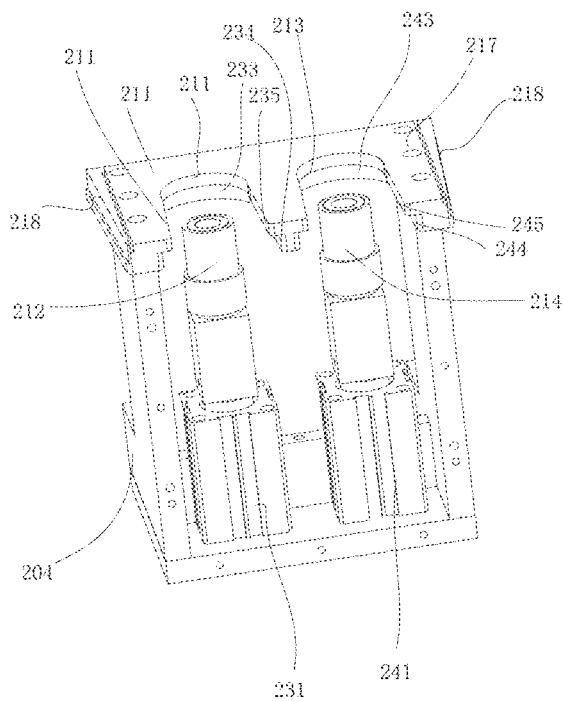
FIG. 11 is a schematic view illustrating the internal structure of a mating head part.

Referring to FIG. 6, FIG. 10, and FIG. 11, the mating head part 210 also includes a mating plate 217, the mating plate 217 includes two guide bayonets 211, 213 for locking the floating sleeve heads 111, 113, and the docking end connectors 212 and 214 can correspondingly pass through two guide bayonets 211 and 213. Specifically, for the two guide bayonets 211, 213, the guide bayonet 211 for passing through the first docking end connector 212 is referred to as the first guide bayonet 211, and the guide bayonet 213 for passing through the second docking end connector 214 is referred to as the second guide bayonet 213. Preferably, the guide bayonet is substantially U-shaped, and it has an inner end formed with a curved surface and two sides 235, 245 having wedge-shaped structures, so that the opening width of the bayonet is gradually reduced from the front end to the inner end. During the process of the mating head part 210 being pushed into the mating space 1100 of the mating bracket 110, such a structure enable the floating sleeve heads 111 and 113 to gradually align with the guide bayonets 211 and 213 without causing collision. In addition, as shown in FIG. 5, the docking device 200 further includes a baffle 220. When the mating head part 210 is pushed into the mating space 1100, the waste collection device 100 pushes the vertical plate 222 of the baffle 220 to make the baffle 220 enter the interior of the docking device 200. After the mating head part 210 is separated from the mating space 1100, the baffle 220 can be manually restored to cover the mating plate 217 and the docking end connectors 212, 214. The docking device 200 also includes a number of second wheels 205.

The mating head part 210 further includes a head base 204, on which the front panel 215 and the mating plate 217 are mounted. The actuating components 231 and 241 are also mounted on the head base 204. Among them, the width of the mating plate 217 is greater than the width of the front panel 215. The mating plate 217 has two correction sides 218 protruding from the two sideplates of the head base 204, and the width of the mating plate 217 is also wider than the head base 204. The correction side 218 is formed into a wedge-shaped structure, that is, the correction side 218 has an inclined surface so that the width of the front portion of the mating plate 217 is smaller than the width of the rear portion. Thus, while the mating head part 210 is pushed into the mating space 1100 of the mating bracket 110, the mating head part 210 and the mating bracket 110 can automatically implement a position correction, meanwhile greatly reducing the risk of damage caused by collision. When the mating head part 210 of the docking device 200 is roughly fitted into the docking space 1100 of the docking bracket 110, the attractor 216 is turned on and an attraction force is instantaneously increased. The correction sides 218 and the guide bayonets 211, 213 will make the mating head part 210 and the mating bracket 110 avoid serious collision even if they are not completely aligned, so that an operating tolerance can be provided in the process of the alignment, thereby avoiding damage to the device. Preferably, the rear portion of the mating plate 217 can form a tight or interference fit with the mating space 1100. A clearance fit is formed between the front portion of the mating plate 217 and the mating space 1100.

Figure 7:
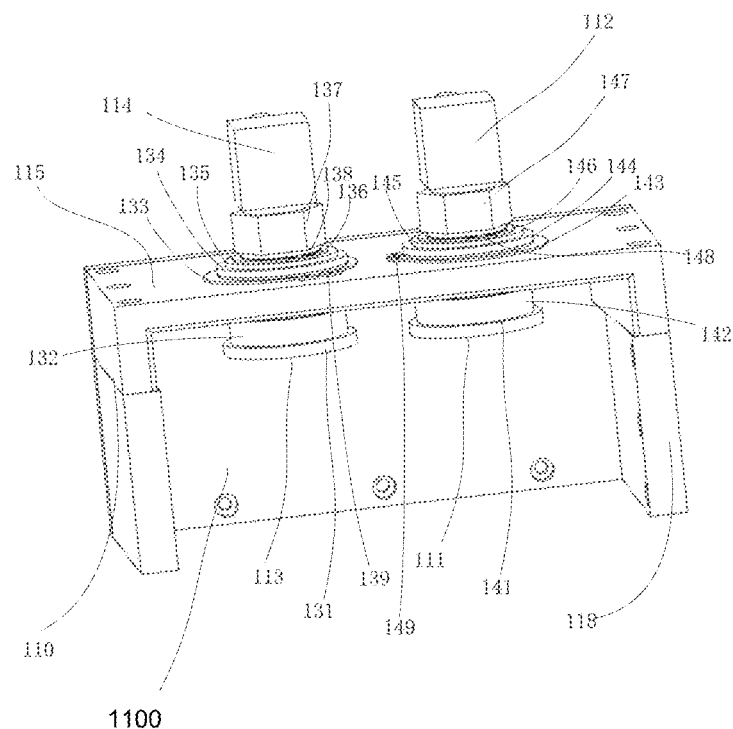
FIG. 7 is a schematic structural view of the mating bracket 110.
Figure 8:
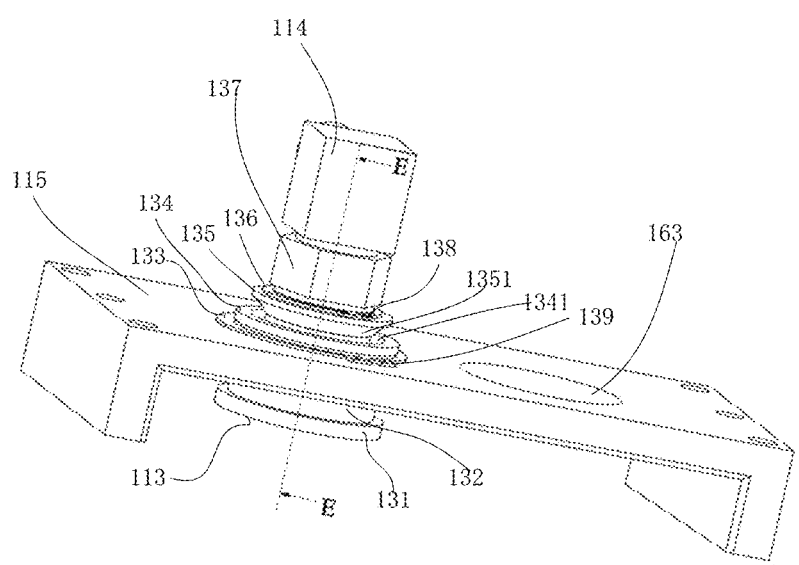
FIG. 8 is a schematic structural view illustrating a second floating sleeve head in a floatingly moveable state.
Figure 9:
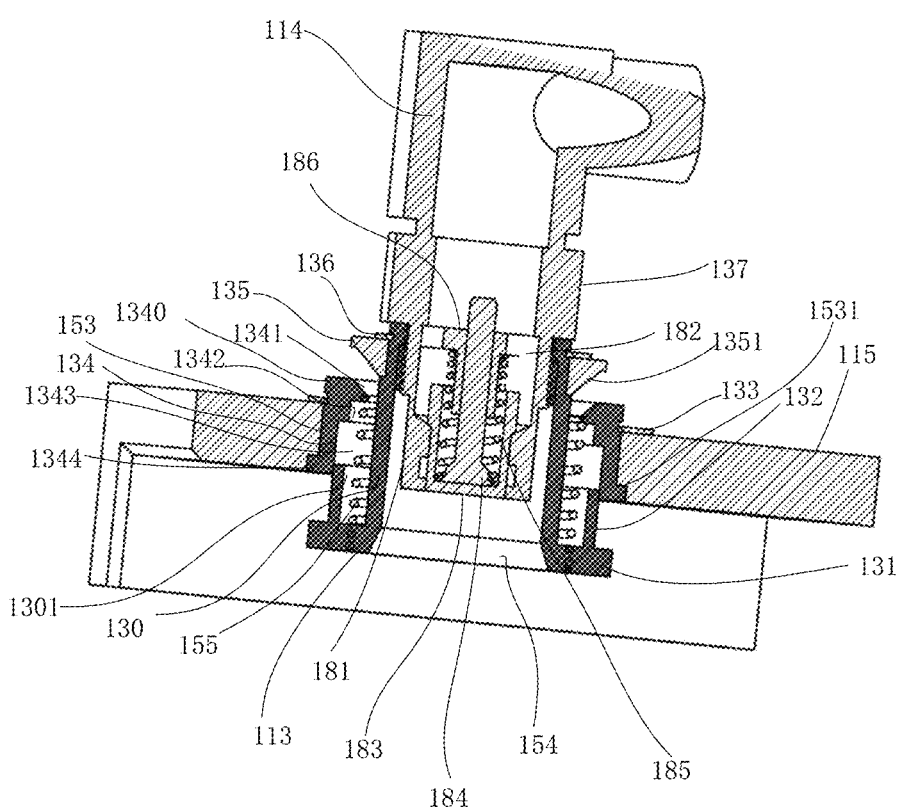
FIG. 9 is a sectional view of the EE cross-section of FIG. 8.

Referring to FIGS. 7-9, FIG. 7 is a schematic structural view of the mating bracket 110, FIG. 8 is a structural schematic view of the second floating sleeve head in a floatingly moveable state, and FIG. 9 is a sectional view of the E-E cross-section of FIG. 8.

As shown in FIG. 7, the mating bracket 110 includes a fixed plate 115 and a guide plate 118. The guide plate 118 and the fixed plate 115 form a mating space 1100 for accommodating the mating head part 210 of the docking device 200. Specifically, the fixed plate 115 is positioned at the top of the mating bracket 110, and the fixed plate 118 is constructed of the back plate and two sideplates of the mating bracket 110. In this embodiment, the fixed plate 115 and the guide plate 118 are separate structures. The two can be mounted and fixed by way of screws or welding. In other embodiments, the fixed plate 115 and the guide plate 118 can be integrally formed.

As shown in FIGS. 8 and 9, the fixed plate 115 is provided with two fixed through holes 153, 163 for mounting two floating sleeve heads 111, 113. The first floating sleeve head 111 and the second floating sleeve head 113 respectively pass through the two fixed through holes 153, 163. Specifically, the fixed plate 115 includes two limiting fixed sleeve 134 and 144 mounted in the two fixed through holes 153, 163 respectively. The two floating sleeve heads 111 and 113 have the same structure. Taking the second floating sleeve head 113 as an example, the floating sleeve head 113 herein refers to the second floating sleeve head 113, which will not be repeatedly described. The floating sleeve head 113 includes a floating sleeve 130 and a first elastic member 155. The floating sleeve 130 is sleeved on the collection end connector 114 and passes through the limiting fixed sleeve 134, and the floating sleeve 130 includes a guide port 154 for guiding the docking end connector 212 and a floatable port 135 for mating with the limiting fixed sleeve 134 in an initial state. When the docking end connector 214 of the docking device 200 is not inserted, the floatable port 135 is mated with the limiting fixed sleeve 134, and the floating sleeve head 113 is located in the initial state. During the process of the insertion of the docking the end connector 214, the floatable port 135 moves relative to the limiting fixed sleeve 134 and guides the docking end connector 214 to align and couple with the corresponding collection end connector 114 so as to form a cleaning passage. The first elastic member 155 is positioned between the guide port 154 and the limiting fixed sleeve 134 and is used to limit the range of movement of the floating sleeve 130 during the process of the insertion of the docking end connector 214 and to return the floating sleeve head 113 to the initial state after the docking end connector 214 is removed.

As shown in FIGS. 8 and 9, taking the limiting fixed sleeve 134 as an example, the limiting fixed sleeve 134 includes a clamping portion 1344, a docking top 1340 for docking with the floatable port 135 in the initial state, a first limiting internal cavity 1342 for limiting one end of the first elastic member 155, and a second limiting internal cavity 1343 for receiving the guide port 154 and limiting the position of the guide port 154. In other embodiments, the first limiting cavity 1342 and the second limiting cavity 1343 may be combined into a single internal cavity. The clamping portion 1344 is used to clamp the lower end of the limiting fixed sleeve 134 into the sleeve locking slot 1531 of the fixed through hole 153. The upper end of the limiting fixed sleeve 134 is fastened by a first lock washer 133, which is interposed between the limiting fixed sleeve 134 and the fixed plate 115 for fastening the limiting fixed sleeve 134. The first lock washer 133 includes a first elastic structure 139. Similarly, the limiting fixed sleeve 144 also has the same structure, the upper end of which is fastened by a first lock washer 143 interposed between the limiting fixed sleeve 144 and the fixed plate 115 for fastening the limiting fixed sleeve 144. The first lock washer 143 includes an elastic structure 149.

Figure 12:
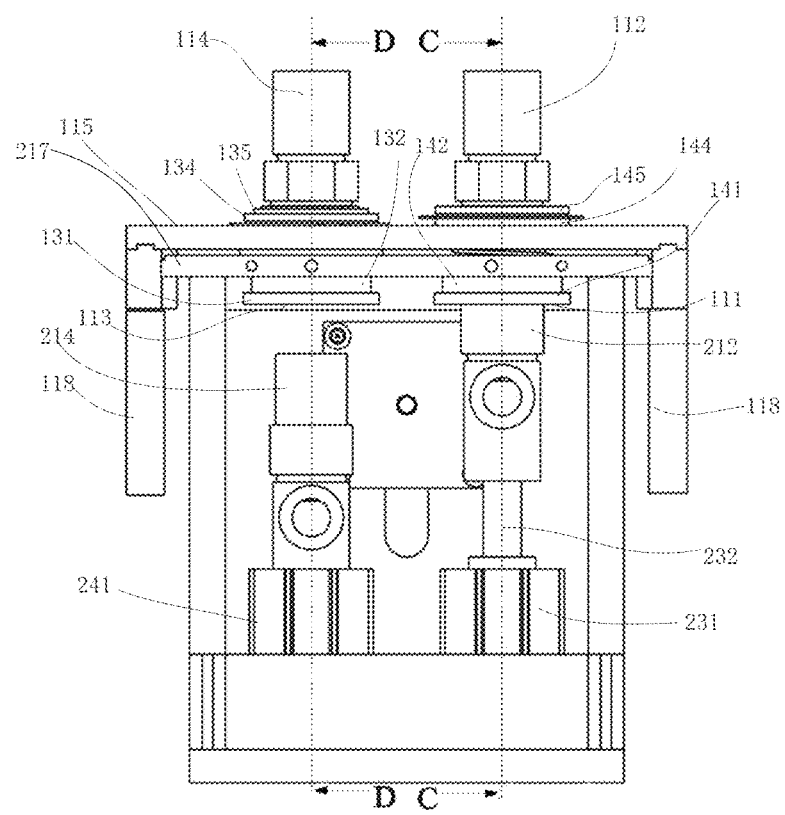
FIG. 12 is a schematic view of the mating head part and the mating bracket after the completion of mating.

The floating sleeve head 113 and the collection end connector 114 are fixedly connected to form a whole. The outer walls of the floating sleeve head 113 and the collection end connector 114 can be integrally formed. The two can also be connected by threads as shown in FIG. 9. After the docking end connector 214 is inserted, the first elastic member 155 is compressed by the push force of the actuating component. At this time, the floating port 135 is separated from the docking top 1340 of the limiting fixed sleeve 134, and the floating sleeve 130 together with the collection end connector 114 connected to it can realize a floating movement under the thrust of the actuating component and the action force of the first elastic member 155, and can swing within a certain range in any direction, so as to implement the guide and position correction to the docking end connector 214 to complete the final docking connection. An outer tube 132 is also disposed at the guide port 135 of the floating sleeve 130, and the outer tube 132 has a limiting edge 131 for mating with the mating head part 210. The diameter of the limiting edge 131 is larger than the diameter of the main body of the outer tube 132, as shown in FIG. 12. FIG. 12 is a schematic view of the mating head part 210 being mated with the mating bracket 110. For the sake of easy illustration, it is assumed that it is in a state where the first collection end connector 112 and the first docking end connector 212 are engaged, while the second collection end connector 114 and the second docking end connector 214 are not engaged. As shown in FIG. 12, the limiting edge 131 is mainly used for mating with the mating plate 217, and after the mating plate 217 is pushed into, the limiting edge 131 is located beneath the mating plate 217, and the main body of the outer tube 132 is received in the guide bayonet 213 of the mating plate 217. When the floating sleeve 130 and the collection end connector 114 connected to it can make a floating movement under the thrust of the actuating component 241 and the action force of the first elastic member 155, and the floating sleeve 130 is raised to the position of the mating plate 217, the limiting edge 131 can limit the position of the floating sleeve 130. As a result, it can prevent an excessive swing of the floating sleeve 130 which increases the difficulty of the docking between the collection end connector 114 and the docking end connector 214. Referring to FIG. 11, the guide bayonet 211 includes a first upper locking groove 233 and a second upper locking groove 234. Referring to FIGS. 11 and 12, the outer tube 132 of the floating sleeve head 111 is contacted with the first upper locking groove 233, that is, the first upper locking groove 233 is used to guide the floating sleeve head 111, and the second upper locking groove 234 can limit the position of the floating sleeve head 111, especially the position of the limiting edge 131 of the floating sleeve head 111. Specifically, the opening of the second upper locking groove 234 is larger than the opening of the first upper locking groove 233. The other guide bayonet 213 also has the same structure, including a first upper locking groove 243 and a second upper locking groove 244.

The outer tube 132 of the floating sleeve head 113 and the floating sleeve 130 form a limiting groove 1301 for defining the other end of the first elastic member 155. The first elastic member 155 is specifically a first spring. As shown in FIG. 9, the first elastic member 155 is sleeved on the floating sleeve 130, and the position of one end of the member 155 is limited by the limiting groove 1301, and the position of the other end is limited by the first limiting internal cavity 1342. The floating sleeve head 111, i.e., the outer tube 142 of the first floating sleeve head 111 and its floating sleeve 140 form a limiting groove 1401 for limiting the other end of the first elastic member 155. The first elastic member 155 is specifically a first spring. As shown in FIG. 9, the first elastic member 155 is sleeved on the floating sleeve 140, and the position of one end of the member is limited by the limiting groove 1401, and the position of the other end is limited by the first limiting internal cavity 1442.

In order to better realize the docking of the mating head part 210 and the mating bracket 110, the docking top 1340 includes a cone-shaped first guide recess 1341, which is used to guide the floatable port 135. The floatable port 135 is a retaining ring detachably fixed to the floating sleeve 130. Correspondingly, the retaining ring 135 includes a cone-shaped guide portion 1351 for mating with the first guide recess 1341. Both the guide portion 1351 and the first guide recess 1341 are similar as to shape and size, and their respective cross-sections are inclined planes. When the floatable port 135 is contacted with the docking top 1340, the smaller diameter plane of the floatable port 135 is contacted with the larger diameter plane of the first guide recess 1341. The gap between the guide portion 1351 and the first guide recess 1341 is a space for correction and adjustment, and the first guide recess 1341 can guide the guide portion 1351 to be gradually aligned. A second lock washer 136 for fastening the retaining ring 135 is also arranged between the floating sleeve 130 and the retaining ring 135, and the second lock washer 136 includes a second elastic structure 138. The guide port 154 is provided with a cone-shaped guide opening so as to better guide the second docking end connector 214 into the second floating sleeve head 113.

Figure 13:
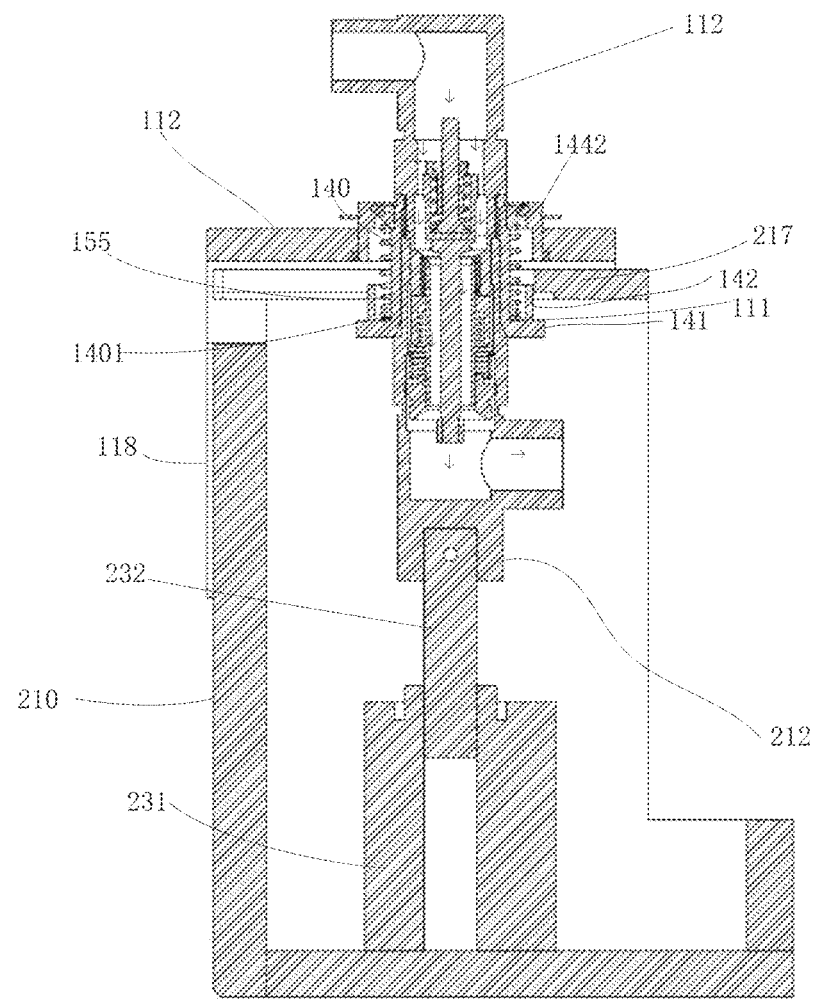
FIG. 13 is a sectional view of the CC cross-section of FIG. 12.
Figure 14:
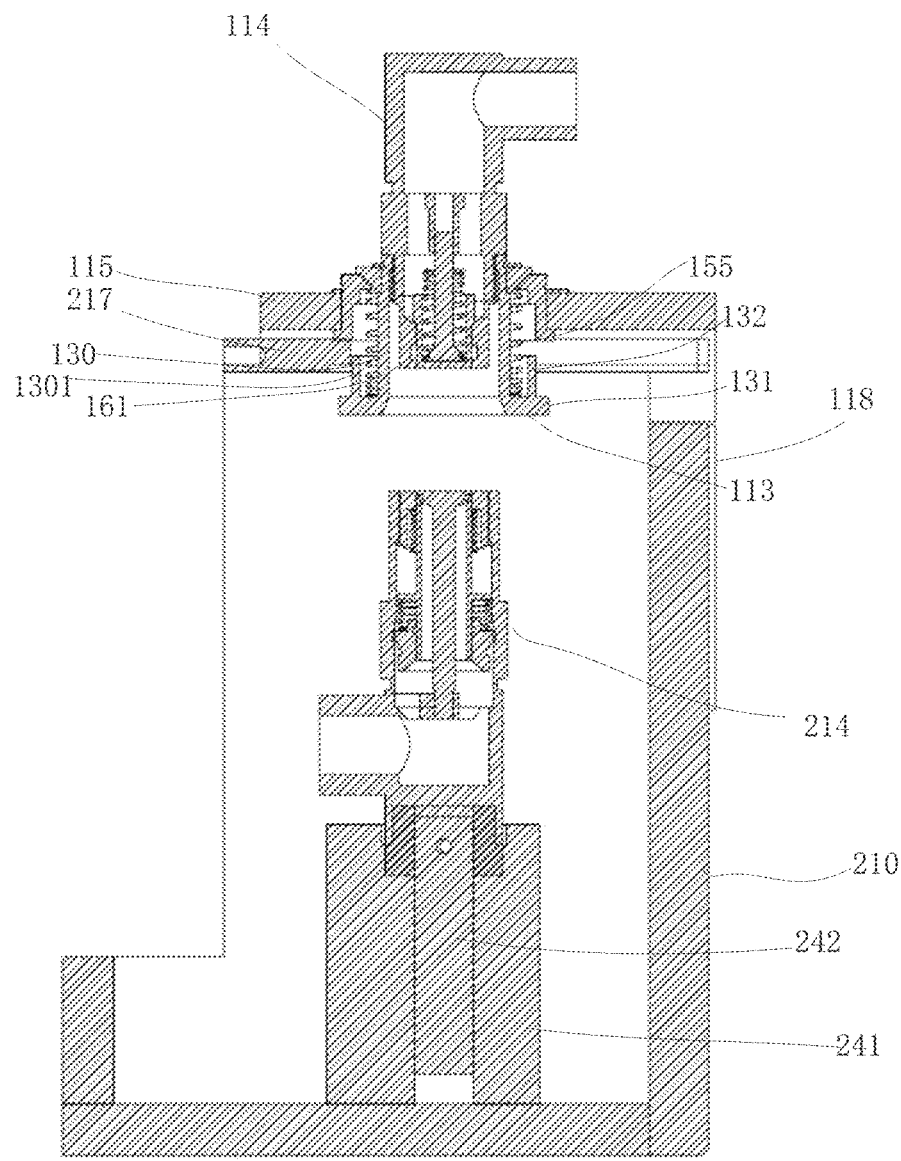
FIG. 14 is a sectional view of the DD cross-section of FIG. 12.

As shown in FIGS. 12-14, after the first docking end connector 212 is inserted into the first floating sleeve 111, the first actuating component 231 pushes the first docking end connector 212 upward through a connecting rod 232. The combination of the first docking end connector 212 and the first collection end connector 112 was implemented after correction so as to form a waste discharge passage indicated by the arrow in FIG. 13. After the second actuating component 241 is turned off, the connecting rod 242 is retracted, and the second docking end connector 214 is separated from the second collection end connector 114. When the second docking end connector 214 is exited from the second floating sleeve 113, and a cleaning passage formed by the second docking end connector 214 and the second collection end connector 114 is interrupted. Taking the second collection end connector 114 as an example, the second collection end connector 114 includes a connector sealing element 183 for automatically sealing and closing a connector port 181 thereof, a connector plunger 184 positioned inside the connector seal 183, and a second elastic member 185 sleeved on the connector plunger 184, wherein one end of the member 185 is positioned in the connector seal 183 and the other end of the member 185 is sleeved on a connector fixed portion 186. The second collection end connector 114 is opened and closed through the connector seal 183, and can be automatically closed through the second elastic member 185.

The beneficial effects by implementing the embodiments of the present disclosure can comprise as follows:

First of all, in the waste collection device according to the embodiment of the present invention, the docking end connectors of the docking device are first mated with the floating sleeve heads, and then the collection end connectors and the docking end connectors are coupled. After the docking end connector is inserted into the corresponding floating sleeve head, the floating sleeve head are floatingly moveable to guide the docking end connector into the floating sleeve head, and the docking end connector is gradually aligned with the collection end connector. Due to the suspension movement of the floating sleeve head, the docking end connector will not cause an impact on the floating sleeve head and will also not bring about a displaced collision with the collection end connector to cause wear, even if the docking end connector and the floating sleeve head are not completely aligned. That is, in the process of the waste collection device being docked to the docking device, there can be a relatively high fault tolerance to position, which can not only improve the accurate rate of docking, but also facilitate user friendly operation, and at the same time it can also reduce the damage caused by the imprecise alignment between the collection end connectors and the docking end connectors.

Secondly, the waste collection device in the embodiments of the invention can have a simple and low complex structure for achieving position guidance and correction, which requires less raw materials, is easy to manufacture, and can reduce costs.

Moreover, the docking device in the embodiments of the invention is provided with a plurality of structures capable of automatically correcting alignment positions in the process of docking with the waste collection device, which can provide a greater fault tolerance to position, improve the accurate rate of docking, and is also easy to operate for users.

The above disclosure has been described with a preferred embodiment according to the present invention and the scope of the present invention cannot be limited by this. Therefore, it is understood that equivalent changes and modifications made according to the claims of the present invention still fall within the scope of the present invention.

We claim:

1. A waste collection device for collecting waste generated in a medical process and docking with a docking device to discharge the waste, the waste collection device comprising:

a portable cart;

at least one waste collection container mounted to the portable cart and configured to store waste generated in a medical process;

a mating bracket mounted to the portable cart and configured to mate with the docking device;

two collection end connectors attached to the mating bracket and connected to the at least one waste collection container, wherein one of the collection end connectors is used to discharge the waste in the waste collection container, and the other is used to introduce a cleaning solution for cleaning the at least one waste collection container; and, two movable sleeve heads mounted to the mating bracket and correspondingly sleeved on the two collection end connectors, wherein the movable sleeve heads are used to guide docking end connectors in the docking device to connect with the corresponding collection end connectors, and the movable sleeve heads are moveable relative to the mating bracket and guide the docking end connectors to engage with the corresponding collection end connectors.

2. The waste collection device according to claim 1, wherein after the docking end connectors and the corresponding collection end connectors are connected, the movable sleeve heads return to an initial position.

3. The waste collection device according to claim 1, wherein the mating bracket includes a fixed plate and a guide plate, and the two movable sleeve heads are mounted to the fixed plate; and the guide plate and the fixed plate form a mating space for receiving a mating head part in the docking device.

4. The waste collection device according to claim 3, wherein the fixed plate includes two fixed through holes for mounting the two movable sleeve heads, and the fixed plate further includes two limiting fixed sleeves mounted in the two fixed through holes respectively.

5. The waste collection device according to claim 4, wherein the movable sleeve head each includes:

a movable sleeve sleeved on the collection end connector and passed through the limiting fixed sleeve, including a guide port for guiding the docking end connector and a movable port for mating with the limiting fixed sleeve in an initial state;

wherein when the docking end connector of the docking device is not inserted, the movable port is mated with the limiting fixed sleeve, and the movable sleeve head is in the initial position; and during the process of the insertion of the docking end connector, the movable port moves relative to the limiting fixed sleeve and guides the docking end connector to align with the corresponding collection end connector;

a first elastic member positioned between the guide port and the limiting fixed sleeve and configured to limit the range of the movement of the movable sleeve during the process of the insertion of the docking end connector and to return the movable sleeve head back to the initial state after the docking end connector is removed.

6. The waste collection device according to claim 4, wherein a first lock washer is interposed between the limiting fixed sleeve and the fixed plate for fastening the limiting fixed sleeve.

7. The waste collection device according to claim 5, wherein the guide port includes a cone-shaped second guide recess.

8. The waste collection device according to claim 5, wherein the movable sleeve is engaged with the collection end connector so that the collection end connector can move along with the movable sleeve.

9. The waste collection device according to claim 5, wherein the first elastic member is a first spring sleeved on the movable sleeve.

10. The waste collection device according to claim 9, wherein a second lock washer is further interposed between the movable sleeve and the retaining ring for fastening the retaining ring.

11. The waste collection device according to claim 5, wherein the limiting fixed sleeve includes a docking top for mating with the movable port in the initial state, and a first limiting internal cavity for limiting one end of the first elastic member, and a second limiting internal cavity for accommodating and limiting the position of the guide port.

12. The waste collection device according to claim 11, wherein an outer tube is further positioned at the guide port of the movable sleeve, and the outer tube has a limiting edge to be mated with the mating head part, and wherein the outer tube and the movable sleeve form a limiting groove for limiting the other end of the first elastic member.

13. The waste collection device according to claim 11, wherein the docking top includes a cone shaped first guide recess for guiding the movable port.

14. The waste collection device according to claim 11, wherein the movable port is a retaining ring detachably fixed to the movable sleeve, and the retaining ring includes a cone-shaped guide portion for mating with the first guide recess.

15. A docking device used in a waste collection and disposal system for transporting waste generated in a medical process collected by the waste collection device in the system, wherein the docking device includes:

a mating head part for mating with a mating bracket in the waste collection device;

at least one actuating component positioned in the mating head part and capable of being freely stretched out and retracted in a particular direction;

two docking end connectors connected to the at least one actuating component, and when the mating head part is aligned with the mating bracket, the actuating component acts to make the docking end connectors in contact with movable sleeve heads in the waste collection device to form a docking connection;

wherein the mating head part includes a mating plate having two guide bayonets for retaining the movable sleeve heads, and the docking end connectors can pass through the guide bayonets.

16. The docking device according to claim 15, wherein the number of the actuating components is two, and they are connected to the two docking end connectors respectively, and the actuating component is a pneumatic pump or a stepper motor.

17. The docking device according to claim 15, wherein the docking device further comprises two guide side plates disposed on both sides of the mating head part for mating with the waste collection device and wherein the guide side plate is provided with a plurality of guide rails, and the guide rails are made of flexible materials.

18. The docking device according to claim 15, wherein the guide bayonet is substantially U-shaped and the mating plate includes two correction sides, which are wedge-shaped structures.

19. The docking device according to claim 18, wherein the guide bayonet has an inner end with a curved surface, and two sides of wedge-shaped structures so that the opening width from the front end to the inner end of the bayonet is gradually reduced.

20. The docking device according to claim 19, wherein the guide bayonet includes a first upper locking groove and a second upper locking groove, the first upper locking groove being configured to guide the movable sleeve, and the second upper locking groove being configured to limit the position of the movable sleeve head.

* * * * *